US008621663B2

(12) United States Patent
Stachler et al.

(10) Patent No.: US 8,621,663 B2
(45) Date of Patent: Jan. 7, 2014

(54) EYE PROTECTORS

(75) Inventors: Thomas H. Stachler, Dayton, OH (US);
Mary I. Grilliot, Dayton, OH (US);
William L. Grilliot, Dayton, OH (US)

(73) Assignee: Honeywell International Inc.,
Morristown, NJ (US)

( * ) Notice: Subject to any disclaimer, the term of this patent is extended or adjusted under 35 U.S.C. 154(b) by 539 days.

(21) Appl. No.: 12/157,485

(22) Filed: Jun. 11, 2008

(65) Prior Publication Data
US 2009/0307817 A1 Dec. 17, 2009

(51) Int. Cl.
*A61F 9/00* (2006.01)
*A61F 9/02* (2006.01)
*G02C 3/00* (2006.01)

(52) U.S. Cl.
USPC ........................................ 2/10; 2/453; 351/155

(58) Field of Classification Search
USPC ........ 2/410, 5, 6.1, 6.2, 6.3, 6.4, 6.5, 6.6, 6.7, 2/425, 15, 10, 12, 13, 9, 209.13, 175.5, 2/175.6; D29/102, 103, 104, 105, 106, D29/107; D2/865, 866, 872, 895; 351/155, 351/156, 157, 47, 48, 57, 58
See application file for complete search history.

(56) References Cited

U.S. PATENT DOCUMENTS

| | | | | |
|---|---|---|---|---|
| 1,298,636 A * | 4/1919 | Altman | | 2/10 |
| 1,514,111 A * | 11/1924 | Sutton | | 2/10 |
| 2,481,960 A * | 9/1949 | Wall et al. | | 2/10 |
| 2,500,280 A * | 3/1950 | Feldman | | 2/10 |
| 2,533,626 A * | 12/1950 | Reiter | | 16/257 |
| 2,648,091 A * | 8/1953 | Jones | | 16/336 |
| 2,677,853 A * | 5/1954 | Ross | | 16/235 |
| 2,717,386 A * | 9/1955 | Linster | | 2/12 |
| 2,998,610 A * | 9/1961 | Spero | | 2/13 |
| 3,298,032 A * | 1/1967 | Sielisch | | 2/13 |
| 3,383,155 A | 5/1968 | Bourke | | |
| 3,383,707 A * | 5/1968 | McNeill | | 2/12 |
| 3,538,509 A * | 11/1970 | Sachse | | 2/12 |
| 4,819,274 A * | 4/1989 | Day | | 2/10 |

(Continued)

OTHER PUBLICATIONS

U.S. Appl. No. 11/974,654, filed Oct. 15, 2007, Stachler et al.

(Continued)

*Primary Examiner* — Shelley Self
*Assistant Examiner* — Jameson Collier
(74) *Attorney, Agent, or Firm* — Wood, Phillips, Katz, Clark & Mortimer

(57) ABSTRACT

An eye protector (16) is provided for mounting on a helmet (10) of the type worn by a firefighter or other emergency worker, the helmet having a brim (14) that projects forwardly and laterally from a lower part of a crown (12). The eye protector (16) includes a bracket (20) mounted to the brim (14), a pair of eye shields (18) movable between a storage position extending along the brim (14) and a usage position extending downward from the brim (14) to shield the eyes of the wearer, and a pair of hinges (22) to connect the eye shields (18) to the bracket (20) for movement between the storage and usage positions. Each of the hinges (22) connects a corresponding one of the eye shields (18) and includes a plurality of aligned hinge openings (24,26) on the eye shield (18) and the bracket (20), a socket (28) on the eye shield (18), and a hinge pin (30) extending through the hinge openings (24,26) and have a first end (32) releasably fixed in the socket (28) and a second end (34) that is exposed outside of the openings (24,26).

6 Claims, 3 Drawing Sheets

(56) References Cited

U.S. PATENT DOCUMENTS

| | | | | |
|---|---|---|---|---|
| 4,843,643 A | * | 7/1989 | Parissenti et al. | 2/13 |
| 4,924,526 A | * | 5/1990 | Parissenti et al. | 2/13 |
| 5,412,812 A | * | 5/1995 | Gatchalian | 2/10 |
| 5,533,208 A | * | 7/1996 | Tonoyan et al. | 2/10 |
| 5,615,413 A | * | 4/1997 | Bower | 2/10 |
| 5,669,071 A | * | 9/1997 | Vu | 2/10 |
| 5,687,420 A | * | 11/1997 | Chong | 2/10 |
| 5,689,827 A | * | 11/1997 | Ryder | 2/10 |
| 5,692,522 A | * | 12/1997 | Landis | 128/857 |
| 5,819,311 A | * | 10/1998 | Lo | 2/12 |
| 6,088,837 A | * | 7/2000 | Baker | 2/195.1 |
| 6,237,147 B1 | * | 5/2001 | Brockman | 2/10 |
| 6,491,390 B1 | * | 12/2002 | Provost | 351/155 |
| 6,530,660 B1 | * | 3/2003 | Chao et al. | 351/63 |
| 7,343,630 B2 | * | 3/2008 | Lee | 2/175.6 |
| 2005/0160511 A1 | * | 7/2005 | Kim | 2/10 |
| 2008/0109927 A1 | * | 5/2008 | Grilliot et al. | 2/10 |
| 2009/0094720 A1 | * | 4/2009 | Stachler et al. | 2/5 |

OTHER PUBLICATIONS

U.S. Appl. No. 12/157,483, filed Jun. 11, 2008, Stachler et al.
U.S. Appl. No. 12/157,539, filed Jun. 11, 2008, Stachler et al.

* cited by examiner

EYE PROTECTORS

CROSS-REFERENCE TO RELATED APPLICATIONS

Not applicable.

FEDERALLY SPONSORED RESEARCH OR DEVELOPMENT

Not applicable.

MICROFICHE/COPYRIGHT REFERENCE

Not applicable.

FIELD OF THE INVENTION

This invention pertains to eye protectors for use with a helmet for a firefighter or other emergency rescue worker.

BACKGROUND OF THE INVENTION

Commonly, a helmet for a firefighter or for an industrial, chemical, or emergency rescue worker has a crown and a brim, which projects forwardly from the crown and which may project in other directions from the crown. Commonly, the helmet is equipped with a pair of eye shields, one for each eye of a wearer, and each of the pair of eye shields is adapted to be manually moved between a storage position and a usage position. In the usage position, but not in the storage position, the eye shield projects downwardly so as to shield a given eye of a wearer against sparks, liquids, particles, and other objects striking the front of the eye shield.

An example of an eye shield, as described in the preceding paragraph, is disclosed in U.S. Pat. No. 3,383,155 to Lester T. Bourke. As disclosed in U.S. Pat. No. 3,383,155, the disclosure of which is incorporated herein by reference, each of the pair of eye shields is mounted to a helmet, beneath a brim projecting forwardly from a crown of the helmet, and each of the pair of eye shields is adapted to be manually flipped between the storage and usage positions and is stable in either of the storage and usage positions. Similar eye shields are available commercially from various sources including Morning Pride Manufacturing, L.L.C. of Dayton, Ohio. While these shields have performed well for their intended purpose, there is always room for improvement.

SUMMARY OF THE INVENTION

In accordance with one feature of the invention, an eye protector is provided for mounting to a protective helmet for use by a firefighter or other emergency worker, the protective helmet having a brim.

According to one feature, the eye protector includes a bracket mounted to the brim, an eye shield movable between a storage position extending along the brim and a usage position extending downward from the brim to shield the eye of a wearer, and a hinge to connect the eye shield to the bracket for movement between the storage and usage positions. The hinge includes a plurality of aligned hinge openings on the eye shield and the bracket, a socket on the eye shield, and a hinge pin extending through the hinge openings and having a first end releasably fixed in the socket and a second end that is exposed outside of the openings.

As one feature, the hinge openings on the eye shield are a unitary part of the eye shield.

According to one feature, the socket is a separate part that is fixed to the eye shield.

In one feature, the hinge openings on the bracket are a unitary part of the bracket.

As one feature, the hinge openings are located between two lateral sides of the eye shield, and the second end of the pin is exposed between one of the lateral sides and one of the hinge openings. As a further feature, the one of the hinge openings is on the eye shield.

In one feature, the first end has an interference fit in the socket.

According to one feature, the eye protector includes a bracket mounted to the brim, a pair of eye shields movable between a storage position extending along the brim and a usage position extending downward from the brim to shield the eyes of a wearer, and a pair of hinges to connect the eye shields to the bracket for movement between the storage and usage positions. Each of the hinges connects a corresponding one of the eye shields and includes a plurality of aligned hinge openings on the eye shield and the bracket, a socket on the eye shield, and a hinge pin extending through the hinge openings and having a first end releasably fixed in the socket and a second end that is exposed outside of the openings.

As one feature, the hinge openings on each of the eye shields are a unitary part of the eye shield.

In one feature, each of the sockets is a separate part that is fixed to the corresponding eye shield.

According to one feature, the hinge opening on the bracket are a unitary part of the bracket.

As one feature, the hinge openings are located between two lateral sides of each of the eye shield, and the second end of each of the pins is exposed between one of the lateral sides of the corresponding eye shield and one of the hinge openings. As a further feature, for each eye shield, the one of the hinge openings is on the eye shield.

In one feature, for each hinge pin, the first end has an interference fit in the corresponding socket.

Other objects, features, and advantages of the invention will become apparent from a review of the entire specification, including the appended claims and drawings.

DETAILED DESCRIPTION OF THE PREFERRED EMBODIMENT

Figure 1:
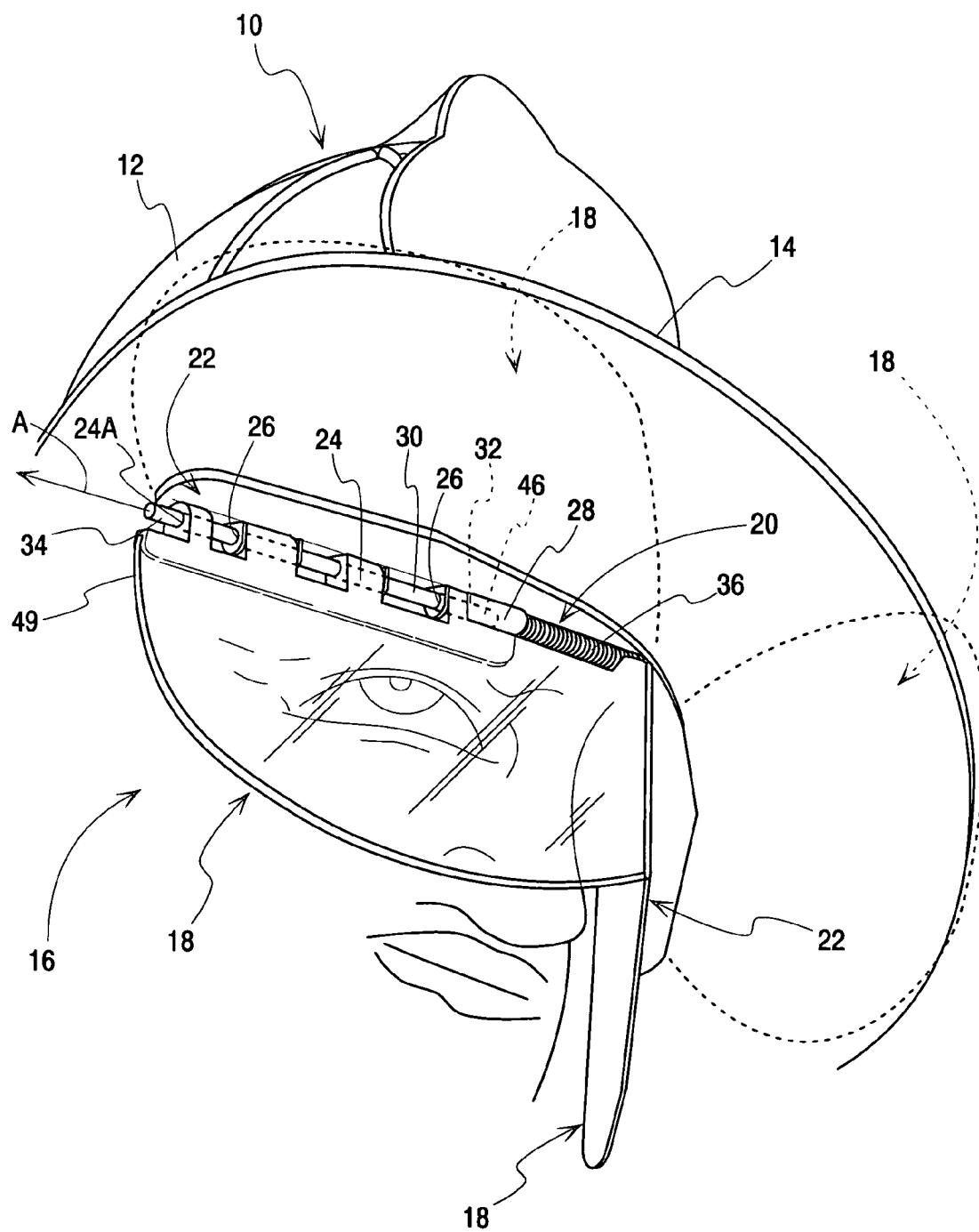
FIG. 1 is a fragmentary, perspective view looking upward toward the front of a helmet equipped with an eye protector embodying the invention.

As shown in FIG. 1, a protective helmet 10 of the type worn by a firefighter or other emergency worker has a crown 12 and a brim 14 that projects forwardly and laterally from the lower part of the crown 12. An eye protector 16 is provided on the helmet 10 in the form of a pair of transparent eye shields 18 that are mounted to the underside of the brim 14 by a bracket 20 for manual movement between a storage position and a usage position. The shields 18 are shown in the usage position in FIG. 1, with each shield 18 extending downward from the brim 14 to shield the eyes of a wearer against sparks, liquids, particles, and other such objects which will strike the front of the shields 18 rather than the eyes of a wearer. In the storage position, each of the shields 18 project forwardly along and beneath the brim 14, as shown in phantom in FIG. 1.

Figure 3:
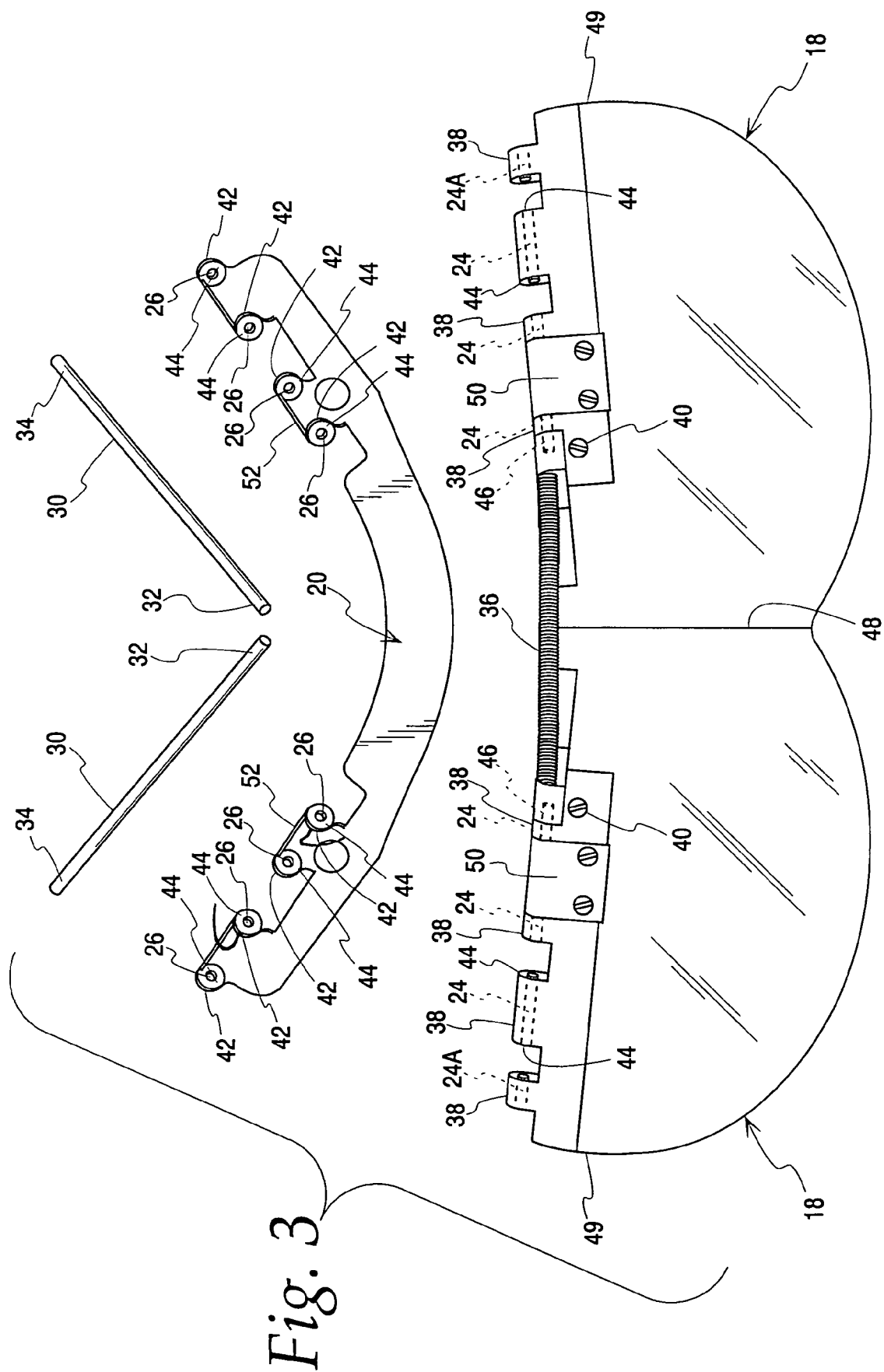
FIG. 3 is an exploded plan view of the eye protector of FIGS. 1 and 2, with the reverse side of a pair of eye shields of the protectors being illustrated.

As shown generally at 22, a pair of hinges are provided to pivotably connect the eye shields 18 to the bracket 20 for movement between the storage and usage position. Each of the hinges 22 connects a corresponding one of the eye shields 18, and as best seen in FIG. 3, includes a plurality of aligned hinge openings 24 on the corresponding eye shield 18, a plurality of aligned hinge openings 26 on the bracket 20, a socket 28 on the corresponding eye shield 18, and a hinge pin 30 extending through the aligned hinge openings 24,26. As best seen in FIG. 1, the hinge pin 30 has a first end 32 releasably fixed in the socket 28 and a second end 34 that is exposed outside of the openings 24 and 26 to allow the pin 30 to be grasped, such as by pliers or the like, for removal in the axial direction A from the socket 28 and the openings 24,26. Preferably, a flexible shaft 36 connects the sockets 28 to each other so that the eye shields 18 move together between the storage and usage position.

Each of the openings 24 extends through a corresponding bearing structure 38 on each of the eye shields 18. Preferably, the bearing structures 38 and their openings 24 are a unitary part of the eye shield 18. However, in some applications, it may be desirable for the bearing structure 38 and openings 24 to be provided as part of a separate bracket component that is attached to the eye shields 18. Preferably, each of the sockets 28 is a separate part that is attached to the eye shield 18 by any suitable means, such as by bonding or by a suitable fastener, for example by such as a rivet fastener 40. However, in some applications it may be desirable for the socket to be made as a unitary part of the shield 18.

Each of the openings 26 are provided in bearing blocks or flanges 42 on the bracket 20 and, preferably, the openings 26 and flanges 42 are a unitary part of the bracket 20. As best seen in FIG. 3, the transverse sides 44 of the bearing structures 38 and flanges 42 abut each other to provide axial alignment of the eye shield 18 with respect to the bracket 20.

Each of the hinge pins 30 is preferably a straight, cylindrical pin having a single diameter, with the end 32 having an interference fit into a conforming bore 46 formed in the socket 28 that allows the pin 30 to be releasably fixed in the socket 28. As another alternative, threads could be provided on the first end 32 and in the bore of the socket 28 to allow for the hinge pin 30 to be releasably fixed in the socket 28.

Figure 2:
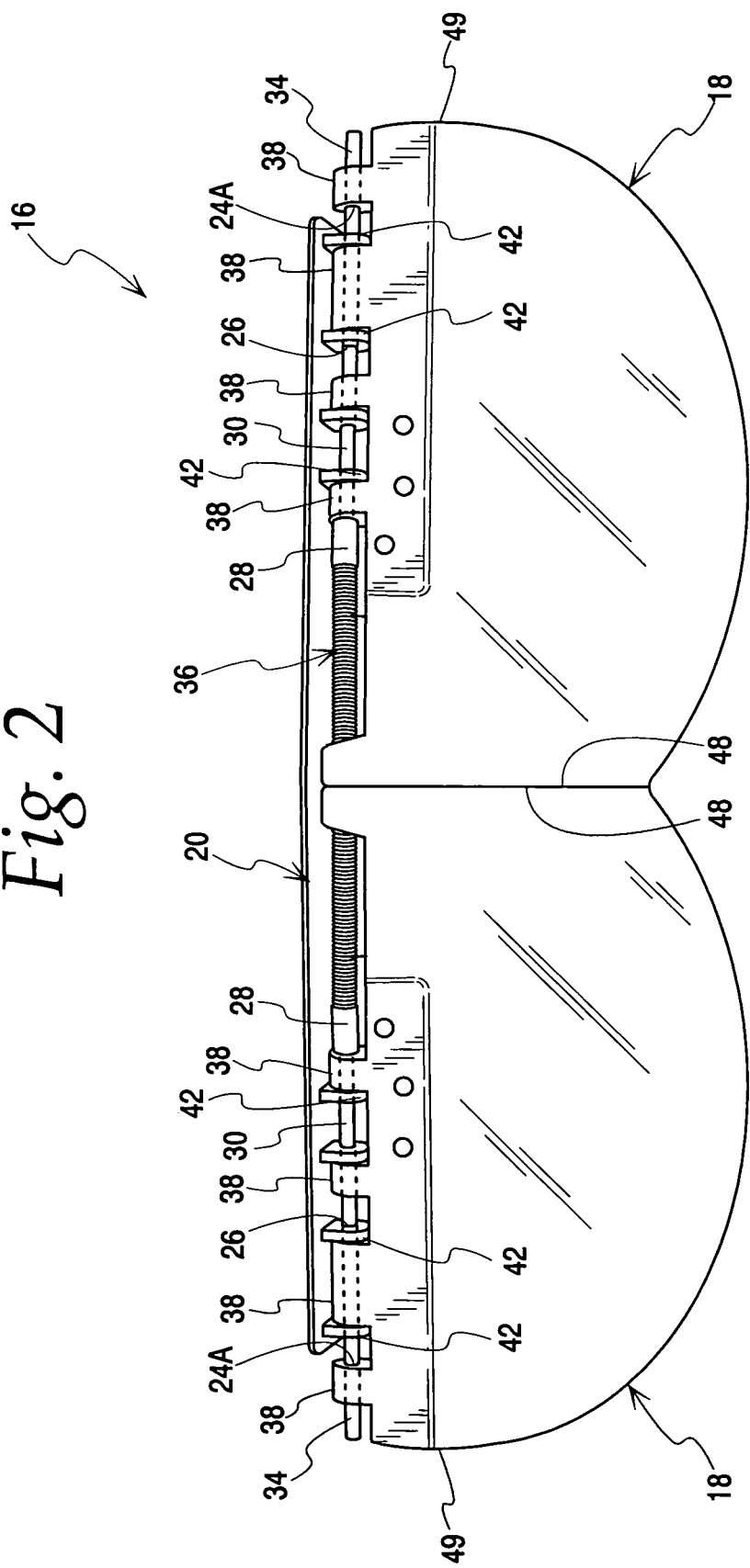
FIG. 2 is an enlarged perspective view showing the eye protector of FIG. 1.

As best seen in FIGS. 2 and 3, each of the eye shields 18 has a pair of lateral sides 48 and 49, with the remainder of the eye shield 18 extending between the sides 48 and 49. Preferably, the openings 24 and 26 are located between the lateral sides 48 and 49 of each of the eye shields 18, and the second end 34 of the pin 30 is exposed between the lateral side 49 and one of the openings 24A, with the exposed length of the end 34 being sufficient for the pin 30 to be grasped for removal.

As best seen in FIG. 3, optionally, a leaf spring 50 may be attached to each of the eye shields 18 for interaction with a corresponding flange 52 on the bracket 20 to urge the eye shield to remain in either the storage or the usage position, when in either position.

It should be appreciated that by removing the pin 30 from the socket 38 and the aligned openings 24,26, the corresponding shield 18 can be removed from the helmet 10 while the bracket 20 remains attached to the brim 14.

The invention claimed is:

1. An eye protector mountable to a protective helmet for use by a firefighter or other emergency worker, the protective helmet having a brim, the eye protector comprising:
a bracket mounted to the brim;
an eye shield movable between a storage position extending along the brim and a usage position extending downward from the brim to shield the eye of a wearer; and
a hinge to connect the eye shield to the bracket for movement between the storage and usage positions, the hinge comprising
a plurality of aligned hinge openings on the eye shield and the bracket,
a socket on the eye shield; and
a hinge pin extending through the hinge openings and having a first end releasably fixed in the socket and a second end that is exposed outside of the openings, wherein the first end has an interference fit into a conforming bore formed in the socket, the interference fit holding the first end against free movement in the socket.

2. The eye protector of claim 1 wherein the interference fit is the only feature that holds the pin in place.

3. An eye protector mountable to a protective helmet for use by a firefighter or other emergency worker, the protective helmet having a brim, the eye protector comprising:
a bracket mounted to the brim;
a pair of eye shields movable between a storage position extending along the brim and a usage position extending downward from the brim to shield the eyes of a wearer; and
a pair of hinges to connect the eye shields to the bracket for movement between the storage and usage positions, each of the hinges connecting a corresponding one of the eye shields and comprising
a plurality of aligned hinge openings on the eye shield and the bracket,
a socket on the eye shield; and
a hinge pin extending through the hinge openings and having a first end releasably fixed in the socket and a second end that is exposed outside of the openings, wherein, for each hinge pin, the first end has an interference fit into a conforming bore formed in the corresponding socket, the interference fit holding the first end against free movement in the socket.

4. The eye protector of claim 3 wherein the interference fit is the only feature that holds the pin in place.

5. An eye protector mountable to a protective helmet for use by a firefighter or other emergency worker, the protective helmet having a brim, the eye protector comprising:
a bracket mounted to the brim;
an eye shield movable between a storage position extending along the brim and a usage position extending downward from the brim to shield the eye of a wearer; and
a hinge to connect the eye shield to the bracket for movement between the storage and usage positions, the hinge comprising
a plurality of aligned hinge openings on the eye shield and the bracket,
a socket on the eye shield;
a hinge pin extending through the hinge openings and having a first end releasably fixed in the socket and a second end that is exposed outside of the openings, the first end and the socket having engaging surfaces that hold the pin against motion in a vector direction extending from the first end toward the second end; and
wherein the engaging surfaces are the only structure that hold the pin against motion in the vector direction extending from the first end toward the second end.

6. An eye protector mountable to a protective helmet for use by a firefighter or other emergency worker, the protective helmet having a brim, the eye protector comprising:

a bracket mounted to the brim;
a pair of eye shields movable between a storage position extending along the brim and a usage position extending downward from the brim to shield the eyes of a wearer; and
a pair of hinges to connect the eye shields to the bracket for movement between the storage and usage positions, each of the hinges connecting a corresponding one of the eye shields and comprising
   a plurality of aligned hinge openings on the eye shield and the bracket,
   a socket on the eye shield;
a hinge pin extending through the hinge openings and having a first end releasably fixed in the socket and a second end that is exposed outside of the openings, the first end and the socket having engaging surfaces that hold the pin against motion in a vector direction extending from the first end toward the second end; and
wherein the engaging surfaces are the only structure that hold the pin against motion in the vector direction extending from the first end toward the second end.

\* \* \* \* \*